United States Patent
Cheng et al.

(10) Patent No.: US 9,980,654 B2
(45) Date of Patent: May 29, 2018

(54) MULTI-FOCUS PHYSIOLOGIC SENSING DEVICE FOR CONDENSING LIGHT

(71) Applicant: AUTOMOTIVE RESEARCH & TEST CENTER, Changhua County (TW)

(72) Inventors: Shun-Wen Cheng, Changhua County (TW); Chun-Yao Shih, Changhua County (TW); Jih-Tao Hsu, Changhua County (TW)

(73) Assignee: Automotive Research & Test Center, Changhua County (TW)

( * ) Notice: Subject to any disclaimer, the term of this patent is extended or adjusted under 35 U.S.C. 154(b) by 341 days.

(21) Appl. No.: 14/972,691

(22) Filed: Dec. 17, 2015

(65) Prior Publication Data

US 2017/0172422 A1   Jun. 22, 2017

(51) Int. Cl.
*A61B 5/02* (2006.01)
*A61B 5/0205* (2006.01)
*H05B 37/02* (2006.01)
*A61B 5/1455* (2006.01)
*A61B 5/145* (2006.01)
*A61B 5/00* (2006.01)
*A61B 5/024* (2006.01)

(52) U.S. Cl.
CPC ........ *A61B 5/0205* (2013.01); *A61B 5/02416* (2013.01); *A61B 5/02427* (2013.01); *A61B 5/1455* (2013.01); *A61B 5/14532* (2013.01); *A61B 5/14552* (2013.01); *A61B 5/6826* (2013.01); *H05B 37/0227* (2013.01); *A61B 5/6824* (2013.01); *A61B 5/6825* (2013.01); *A61B 5/6838* (2013.01); *A61B 5/7203* (2013.01); *A61B 2562/0233* (2013.01)

(58) Field of Classification Search
CPC ........................................................ A61B 6/00
See application file for complete search history.

(56) References Cited

U.S. PATENT DOCUMENTS

| | | | |
|---|---|---|---|
| 5,995,856 A | 11/1999 | Mannheimer et al. | |
| 6,819,687 B1* | 11/2004 | Fein | G02B 6/102 372/6 |
| 2009/0018452 A1* | 1/2009 | Sugiura | A61B 5/02433 600/476 |
| 2016/0097511 A1* | 4/2016 | Catalano | F21V 7/048 362/223 |

* cited by examiner

Primary Examiner — Luke D Ratcliffe
(74) Attorney, Agent, or Firm — Rosenberg, Klein & Lee (57) ABSTRACT

A multi-focus physiologic sensing device for condensing light is disclosed, comprises a multi-focus condenser has one first ellipse reflection member, and one second ellipse reflection member is arranged at an end of the first ellipse reflection member. The first ellipse reflection member has a first focus point thereon. The second ellipse reflection member has two second focus points thereon. A boundary between the first ellipse reflection member and the second ellipse reflection member has a first confocal point. Two lighting elements are respectively arranged on the two second focus points to generate light sources, that focus light on the first confocal point through the second ellipse reflection member, and then the detected object reflects the detected light source back to the first confocal point. Then, the detected light source is passes through the sensor from the first focus.

15 Claims, 8 Drawing Sheets

MULTI-FOCUS PHYSIOLOGIC SENSING DEVICE FOR CONDENSING LIGHT

BACKGROUND OF THE INVENTION

Field of the Invention

The present invention relates to a physiologic detection device, particularly to a multi-focus physiologic sensing device for efficiently condensing light.

Description of the Related Art

With technological advancements, in recent years the development of wearable physiologic detection devices is more and more popular, such as physiologic sensing watches. An optical detection method is generally used in the traditional technology. A lighting element is used to generate a light source which is incident on a detected skin, and then the method senses the optical signals reflected by the skin. The method analyzes the intensity variation of the light with different wavelengths after penetrating physiologic tissue, and uses the variation to figure out physiologic values such as heart rates, blood oxygen, and blood sugar. However, if the intensity of the light source is insufficient, the light source is easily affected by noise of environment light without penetrating the skin and the physiologic tissue. As a result, the physiologic values will not be precisely measured.

In order to increase the condensing efficiency of light, a condenser is added to increase the intensity of light, thereby increasing a signal to noise (S/N) ratio. The condenser used in the prior techniques has a small light-collection angle, such as a Fresnel lens, whereby the condensing efficiency is not improved efficiently. Besides, when heart rates, blood oxygen, and blood sugar are measured, the light sources with different wavelengths are used. If the condenser with one focus is merely used, the light sources with different wavelengths cannot simultaneously be analyzed, which leads to measuring an imprecise physiologic state.

Figure 1:
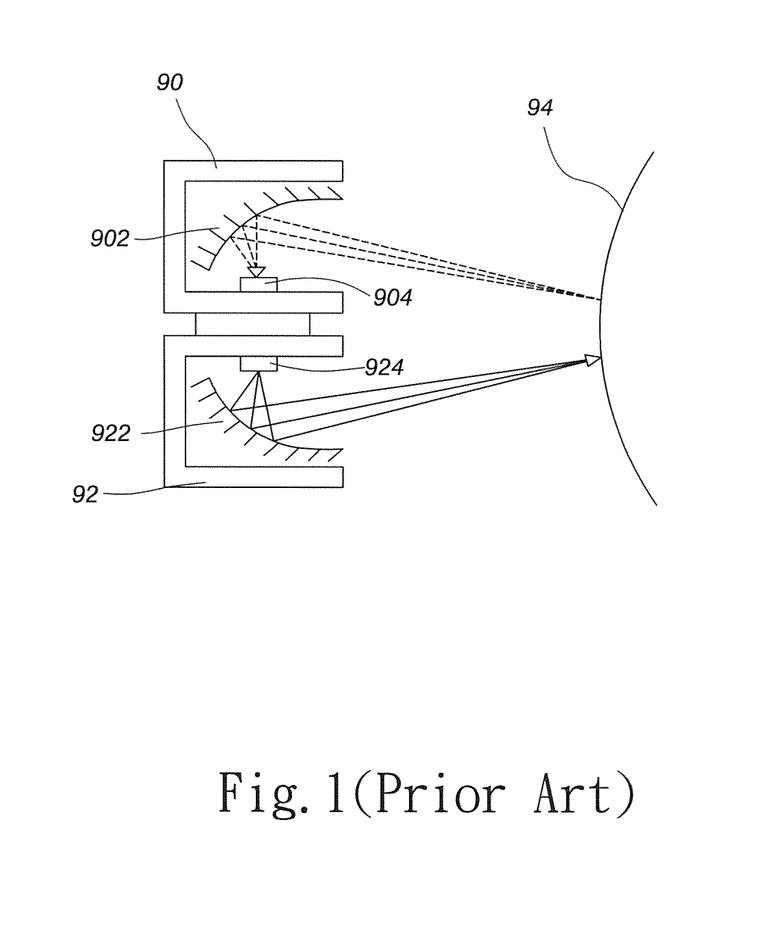
FIG. 1 is a diagram schematically showing a physiologic detection device in the traditional technology.

Take a U.S. Pat. No. 5,995,856 for example. Refer to FIG. 1, which shows an upper casing 90 and a lower casing 92 under the upper casing 90. The upper casing 90 has an upper concave mirror 902 and a physiologic sensor 904. The lower casing 92 has a lower concave 922 and a lighting element 924. The lighting element 924 projects light on the lower concave 922. The lower concave 922 condenses and reflects the light to a detected skin 94. Then, the detected skin 94 reflects the light to the upper concave mirror 902 to project the light on the physiologic sensor 904 for physiologic state detection. However, the US patent does not mention that the condensing efficiency is increased by adjusting curvature of a reflection surface of the concave mirror. In addition, measuring various physiologic signals requires processing and sensing the light sources with at least 2~3 different wavelengths. Nevertheless, the US patent cannot detect different physiologic signals by simultaneously using the light sources with different wavelengths. Accordingly, the US patent cannot measure physiologic signals such as heart rates, blood oxygen, and blood sugar.

To overcome the abovementioned problems, the present invention provides a multi-focus physiologic sensing device for condensing light, so as to solve the afore-mentioned problems of the prior art.

SUMMARY OF THE INVENTION

A primary objective of the present invention is to provide a multi-focus physiologic sensing device for condensing light, which efficiently increases light-condensing intensity and a light-collection angle, and which simultaneously uses the light sources with different wavelengths to focus on a detected skin due to several incident light focuses, and which utilizes variation of intensity of the light penetrating the skin to detect various physiologic signals.

Another objective of the present invention is to provide a multi-focus physiologic sensing device for condensing light, which increases productivity and light-condensing efficiency greatly.

To achieve the abovementioned objectives, the present invention provides a multi-focus physiologic sensing device for condensing light, which comprises at least two lighting elements, and each lighting element generates a light source. At least one multi-focus condenser has at least one first ellipse reflection member and at least one second ellipse reflection member. The second ellipse reflection member is arranged at an end of the first ellipse reflection member. The first ellipse reflection member has a first transparent plane and a first focus point thereon. A sensor is arranged on the first focus point. A boundary between the first ellipse reflection member being confocal with the second ellipse reflection member has a first confocal point, and a detected object is arranged on the first confocal point. The second ellipse reflection member has a second transparent plane and at least two second focus points thereon. The two lighting elements are respectively arranged on the two second focus points to generate the two light sources. The two light sources focus light on the first confocal point through the second ellipse reflection member whereby the light is incident on the detected object to form a detected light source, and then the detected object reflects the detected light source back to the first confocal point. Then, after the detected light source is reflected by the first ellipse reflection member, the detected light source is passes through the sensor from the first focus point, so as to detect a physiologic state.

Below, the embodiments are described in detail in cooperation with the drawings to make easily understood the technical contents, characteristics and accomplishments of the present invention.

DETAILED DESCRIPTION OF THE INVENTION

Figure 2:
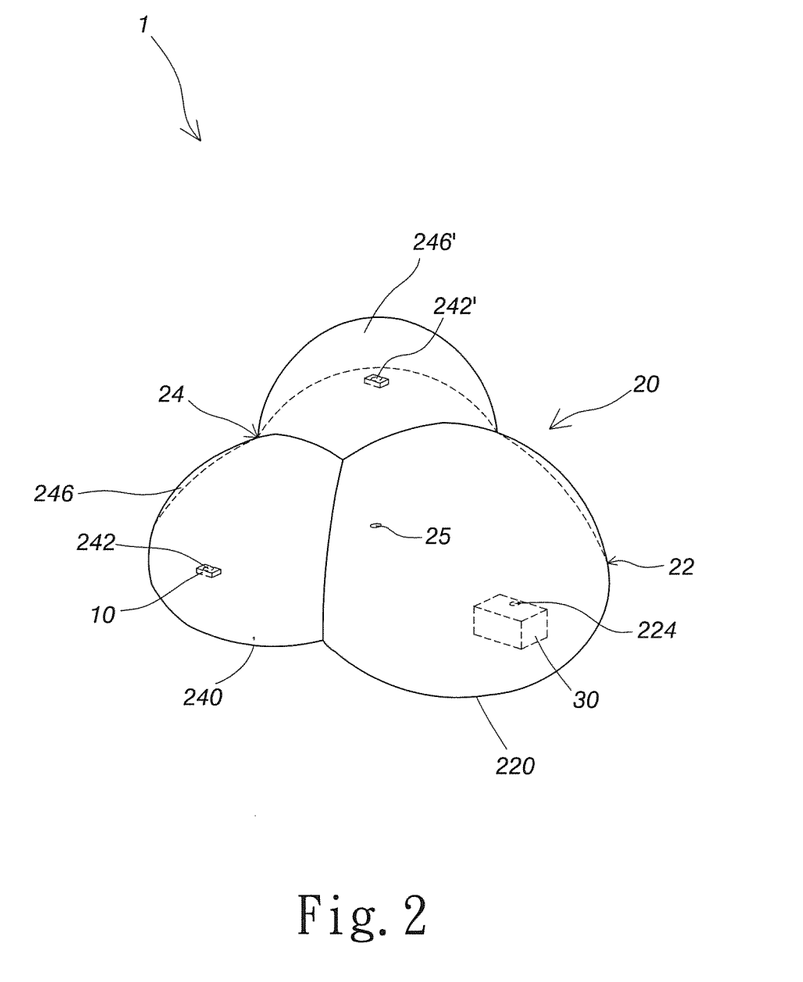
FIG. 2 is a three-dimensional diagram showing a multi-focus physiologic sensing device for condensing light according to the first embodiment of the present invention.

Refer to FIG. 2. The multi-focus physiologic sensing device 1 for condensing light comprises at least two lighting elements 10. Each lighting element 10 generates a light source. At least one multi-focus condenser 20 has at least one first ellipse reflection member 22 and at least one second ellipse reflection member 24. The second ellipse reflection member 24 is arranged at an end of the first ellipse reflection member 22. The second ellipse reflection member 24 is tilted upward with respect to the first ellipse reflection member 22. The second ellipse reflection member 24 is inclined at an angle of 1~15 degrees, preferably an angle of 3~5 degrees. The first ellipse reflection member 22 and the second ellipse reflection member 24 are integrally formed. A lower surface of the first ellipse reflection member 22 has a first transparent plane 220 and a first focus point 224 thereon. A boundary between the first ellipse reflection member 22 and the second ellipse reflection member 24 has a first confocal point 25. In the embodiment, the second ellipse reflection member 24 has two first ellipse reflection parts 246 and 246'. Lower surfaces of the first ellipse reflection parts 246 and 246' has a second transparent plane 240. The first ellipse reflection part 246 has a second focus point 242 on the second transparent plane 240. The first ellipse reflection part 246' has a second focus point 242' on the second transparent plane 240. The two lighting elements 10 are respectively arranged on the two second focus points 242 and 242' to generate two light sources, whereby the light sources pass into the second ellipse reflection member 24 from the second focus points 242 and 242'. At least one sensor 30 is arranged on the first focus point 224 of the first ellipse reflection member 22 of the multi-focus condenser 20. The sensor 30 is realized with a photodiode (PD), a photo transistor, or a charge-coupled device (CCD).

Figure 3:
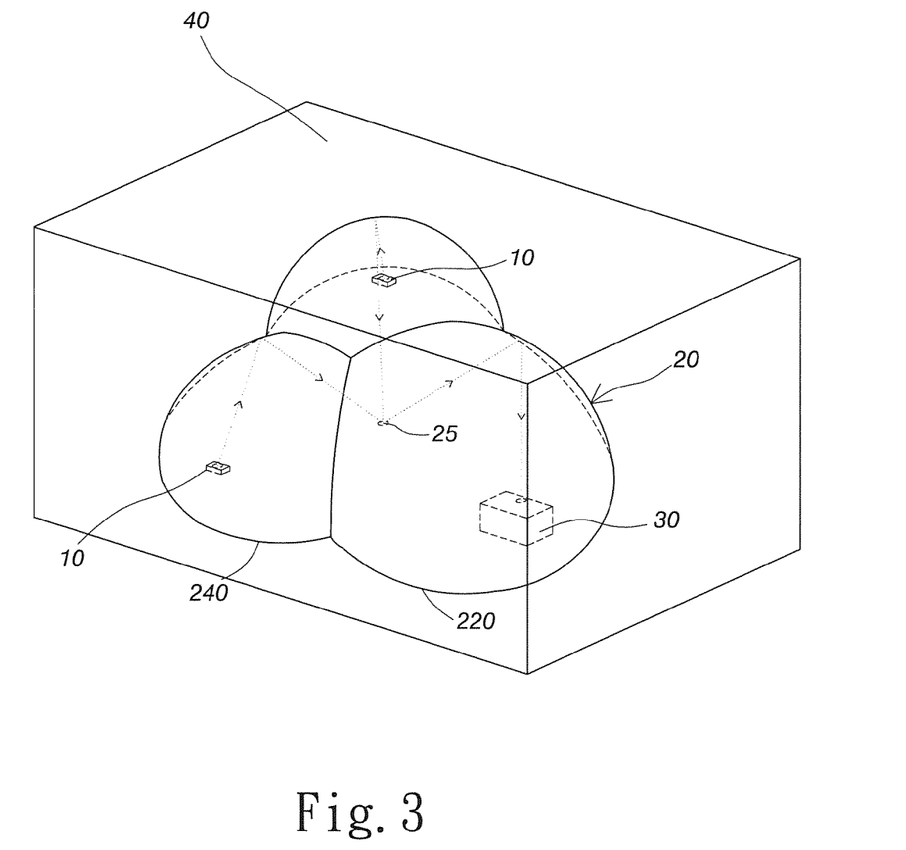
FIG. 3 is a diagram schematically showing a multi-focus physiologic sensing device for condensing light encased by a casing according to the first embodiment of the present invention.
Figure 4:
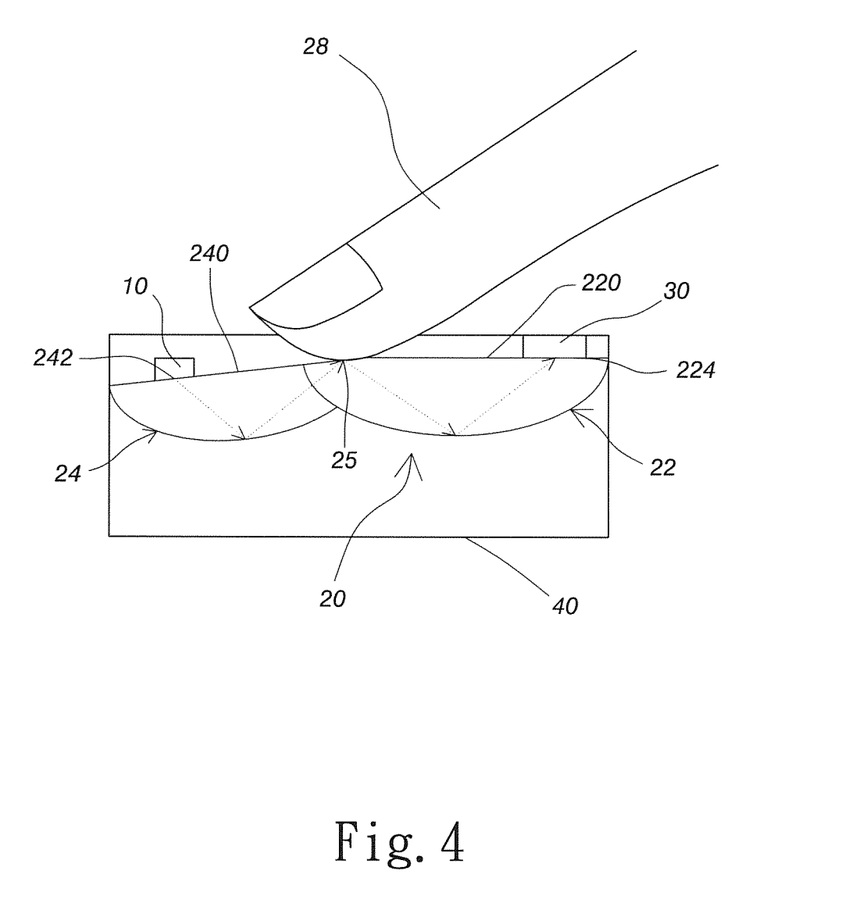
FIG. 4 is a lateral perspective view showing a multi-focus physiologic sensing device for condensing light encased by the casing according to the first embodiment of the present invention.
Figure 5:
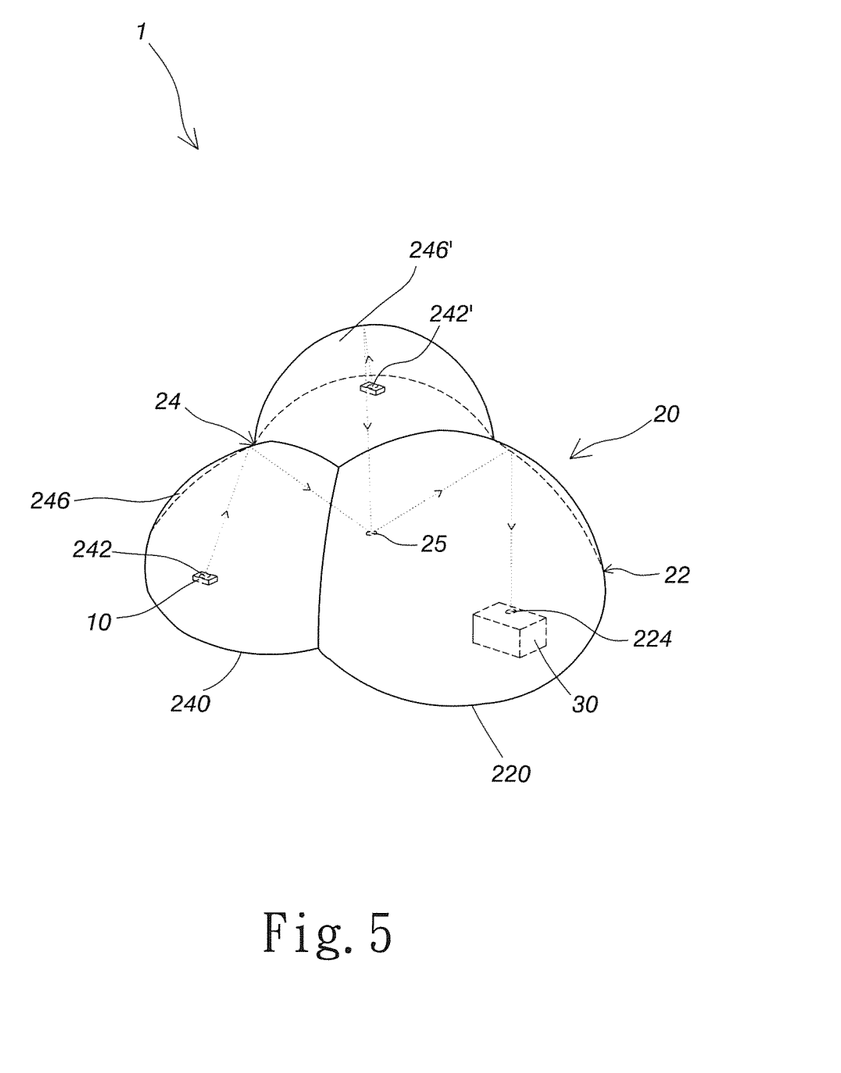
FIG. 5 is a diagram schematically showing light refraction according to the first embodiment of the present invention.

Besides, refer to FIG. 3 and FIG. 4. The present invention further comprises a casing 40 encasing the lighting elements 10, the multi-focus condenser 20 and the sensor 30 and exposing the first confocal point 25. A detected object 28 such a finger or a skin of a wrist is arranged on the first confocal point 25 to be detected. In addition, two sides of the casing 40 are provided to bands (not shown) for installation. In this way, the multi-focus physiologic sensing device 1 for condensing light can be bound to a hand of a user, so as to measure a physiologic signal for the skin of the wrist of the hand. Alternatively, the multi-focus physiologic sensing device 1 for condensing light can be installed on a steering wheel of a car. When a driver drives his car, the skin of the finger of the driver directly touches the measuring point of the multi-focus physiologic sensing device 1 for condensing light to immediately detect a physiologic state. When the physiologic state is not good, the driver is rapidly warned.

Then, refer to FIGS. 2~5. The light routes of the abovementioned embodiment are explained as below. Firstly, when measuring the physiologic signal, the detected object 28 is provided, such as the finger of the user. The detected object 28 is arranged on the first confocal point 25 of the multi-focus condenser 20. Then, the two lighting elements 10 generate the two light sources to pass into the first ellipse reflection parts 246 and 246' from the second focus points 242 and 242'. Then, the two light sources reach the curved surfaces of the first ellipse reflection parts 246 and 246'. The curved surfaces of the first ellipse reflection parts 246 and 246' reflect the two light sources and focus them on the first confocal point 25, and then the light sources are incident on the detected object 28 to form a detected light source. Then, the detected object 28 reflects the detected light source to the first confocal point 25. Then, the first ellipse reflection member 22 receives the detected light source from the first confocal point 25. The curved surface of the first ellipse reflection member 22 reflects the detected light source to the first focus point 224. The detected light source is transmitted from the first focus point 224 to the sensor 30. The sensor 30 detects physiologic parameters of the user according to the detected light source. The lighting elements 10, for example, but not limited to light emitting diodes (LEDs), surface-mounted-device light-emitting diodes (SMD LEDs), laser diodes (LDs), red light lighting elements, green light lighting elements, or infrared light lighting elements, are used. The infrared light lighting element emits light having a wavelength of 1000 nm~1700 nm and used to measure blood sugar. The green light lighting element emits light having a wavelength of 500 nm~560 nm and used to measure a heart rate. The red light lighting element emits light having a wavelength of 600 nm~700 nm or 900 nm~1000 nm and used to measure blood oxygen. The present invention uses the lighting elements 10 with different wavelengths to measure various physiologic signals, and replaces the lighting elements 10 according to the requirement of measuring physiologic signals.

Figure 6:
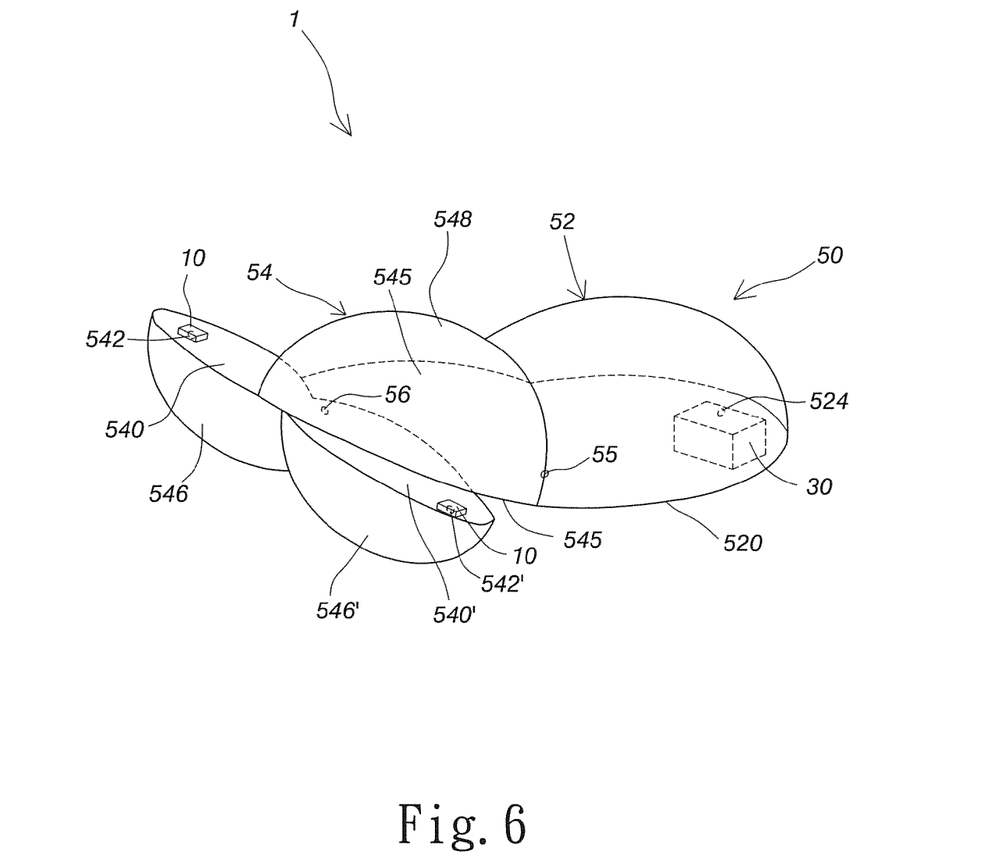
FIG. 6 is a three-dimensional diagram showing a multi-focus physiologic sensing device for condensing light according to the second embodiment of the present invention.

In addition to the abovementioned embodiment, the multi-focus physiologic sensing device 1 for condensing light of the present invention is shown FIG. 6. The multi-focus physiologic sensing device 1 for condensing light comprises at least one multi-focus condenser 50 has at least one first ellipse reflection member 52 and at least one second ellipse reflection member 54. The second ellipse reflection member 54 is arranged at an end of the first ellipse reflection member 52. The second ellipse reflection member 54 is tilted upward with respect to the first ellipse reflection member 52. The second ellipse reflection member 54 is inclined at an angle of 1~15 degrees, preferably an angle of 3~5 degrees. The first ellipse reflection member 52 and the second ellipse reflection member 54 are integrally formed. A lower surface of the first ellipse reflection member 52 has a first transparent plane 520 and a first focus point 524 thereon. A boundary between the first ellipse reflection member 52 and the second ellipse reflection member 54 has a first confocal point 55. In the embodiment, the second ellipse reflection member 54 has two first ellipse reflection parts 546 and 546' and a second ellipse reflection part 548. The curved surface of the first ellipse reflection part 546 is identical to the curved surface of the second ellipse reflection part 548. Each first ellipse reflection part 546 and 546' has one second transparent plane 540 and 540'. The first ellipse reflection part 546 and 546' has second focus points 542 and 542'. The second focus points 542 and 542' at both ends of the second transparent plane 540 and 540'. Two lighting elements 10 are respectively arranged on the two second focus points 542 and 542' to generate two light sources, whereby the light sources pass into the second ellipse reflection member 54 from the second focus points 542 and 542'. The second ellipse reflection part 548 is arranged at an end of the first ellipse reflection member 52. A lower surface of the second ellipse reflection part 548 has a third transparent plane 545. A second confocal point 56 of the second ellipse reflection member 54 on the third transparent plane 545 The two first ellipse reflection parts 546 and 546' are inversely arranged on the second ellipse reflection part 548 to connect the second transparent planes 540 and 540' with the third transparent plane 545. At least one sensor 30 is arranged on the first focus point 524 of the first ellipse reflection member 52 of the multi-focus condenser 50.

Figure 7:
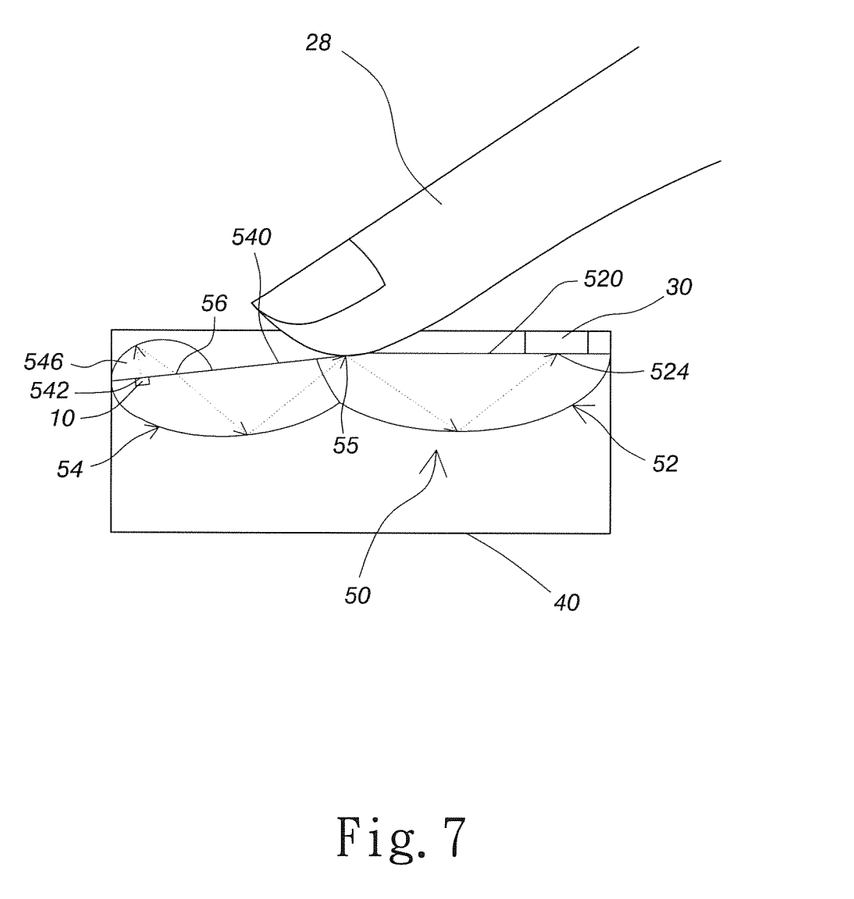
FIG. 7 is a lateral perspective view showing a multi-focus physiologic sensing device for condensing light encased by a casing according to the second embodiment of the present invention.

Then, refer to FIG. 7. The present invention further comprises a casing 40 encasing the lighting elements 10, the multi-focus condenser 50 and the sensor 30 and exposing the first confocal point 55. A detected object 28 such a finger or a skin of a wrist is arranged on the first confocal point 55 to be detected. The other technical features are the same to those of the first embodiment so will not be reiterated.

Figure 8:
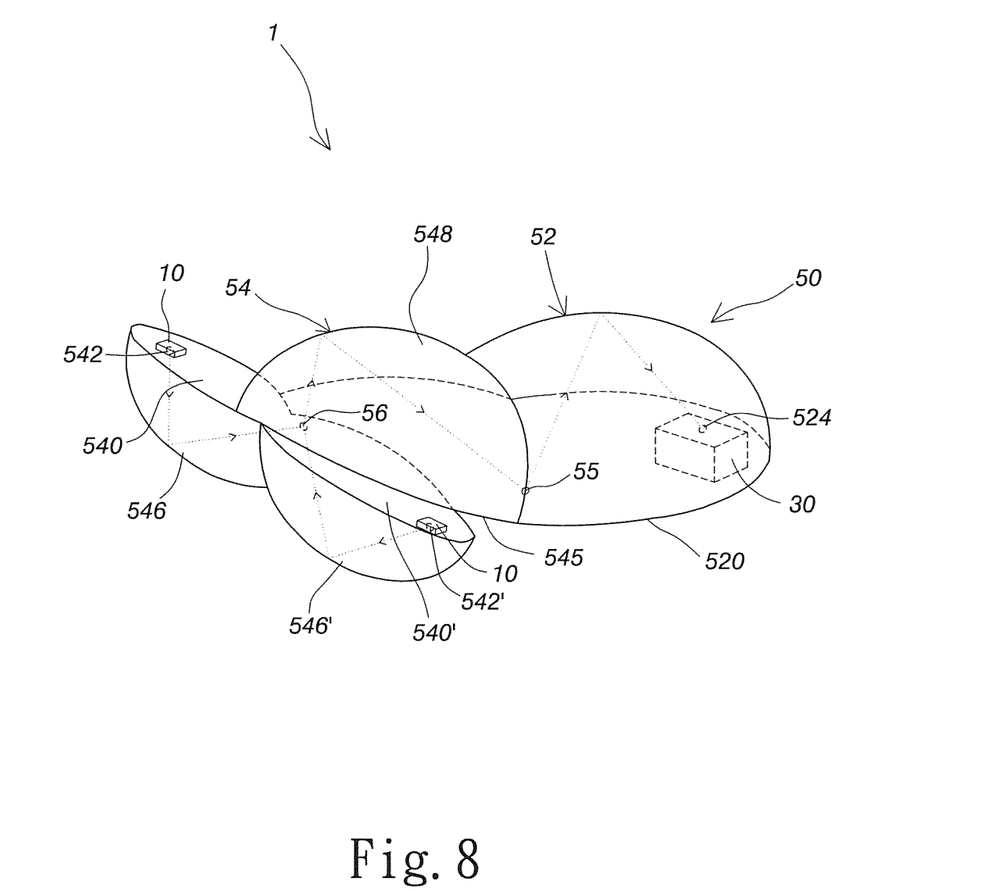
FIG. 8 is a diagram schematically showing light refraction according to the second embodiment of the present invention.

Then, refer to FIGS. 6~8. The light routes of the second embodiment are explained as below. Firstly, when measuring the physiologic signal, the detected object 28 is provided, such as the finger of the user. The detected object 28 is arranged on the first confocal point 55 of the multi-focus condenser 50. Then, the two lighting elements 10 generate the two light sources to pass into the first ellipse reflection parts 546 and 546' from the second focus points 542 and 542'. Then, the two light sources reach the curved surfaces of the first ellipse reflection parts 546 and 546'. The curved surfaces of the first ellipse reflection parts 546 and 546' reflect the two light sources and focus them on the second confocal point 55, and then the light sources are transmitted to the second ellipse reflection part 548. The second ellipse reflection part 548 reflects the light sources to the first confocal point 55 whereby the light sources are passes through the detected object 28 from the first confocal point 55, so as to form a detected light source. Then, the detected object 28 reflects the detected light source to the first confocal point 55. Then, the first ellipse reflection member 52 receives the detected light source from the first confocal point 55. The curved surface of the first ellipse reflection member 52 reflects the detected light source to the first focus point 524. The detected light source is transmitted from the first focus point 524 to the sensor 30. The sensor 30 detects physiologic parameters of the user according to the detected light source. The lighting elements are the same to those of the first embodiment so will not be reiterated.

In conclusion, the present invention possesses a simple structure to greatly improve productivity light-condensing efficiency, efficiently increases light-condensing intensity and a light-collection angle, simultaneously uses the light sources with different wavelengths to focus on a detected skin due to several incident light focuses, and utilizes variation of intensity of the light penetrating the skin to detect various physiologic signals.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A multi-focus physiologic sensing device for condensing light comprising:
at least two lighting elements each generating a light source;
at least one multi-focus condenser having at least one first ellipse reflection member and at least one second ellipse reflection member, and said second ellipse reflection member is arranged at an end of said first ellipse reflection member, and said first ellipse reflection member has a first transparent plane and a first focus point thereon, and said second ellipse reflection member has a second transparent plane and at least two second focus points thereon, and a boundary between said first ellipse reflection member and said second ellipse reflection member has a first confocal point, and said two lighting elements are respectively arranged on said two second focus points to generate said two light sources, and said two light sources focus light on said first confocal point through said second ellipse reflection member whereby said light is incident on a detected object to form a detected light source, and then said detected object reflects said detected light source back to said first confocal point whereby said detected light source is emitted exit from said first focus point after reflection; and
at least one sensor arranged on said first focus point of said multi-focus condenser and receiving said detected light source to detect a physiologic state.

2. The multi-focus physiologic sensing device for condensing light of claim 1, wherein said second ellipse reflection member of said multi-focus condenser further comprises two first ellipse reflection parts, and an end of each of said first ellipse reflection parts has one of said second focus points.

3. The multi-focus physiologic sensing device for condensing light of claim 1, wherein said first ellipse reflection member and said second ellipse reflection member are integrally formed.

4. The multi-focus physiologic sensing device for condensing light of claim 1, wherein said detected object is arranged on said first confocal point.

5. The multi-focus physiologic sensing device for condensing light of claim 1, wherein said second ellipse reflection member is tilted upward with respect to said first ellipse reflection member.

6. The multi-focus physiologic sensing device for condensing light of claim 5, wherein said second ellipse reflection member is inclined at an angle of 1~15 degrees.

7. The multi-focus physiologic sensing device for condensing light of claim 1, wherein said second ellipse reflection member further comprises two first ellipse reflection parts and a second ellipse reflection part, and each of said first ellipse reflection parts has said second transparent plane and one of said second focus points thereon, and said second ellipse reflection part has a third transparent plane and a second confocal point, and said second ellipse reflection part is arranged at an end of said first ellipse reflection member, and said two first ellipse reflection parts are inversely arranged on said second ellipse reflection part to connect said second transparent planes with said third transparent plane, and said second focus points respectively receive said light sources to pass said light sources into said first ellipse reflection parts, and then said first ellipse reflection parts focus said light sources on said second confocal point, and then reflect said light sources to said first ellipse reflection member, and said light sources are passes through said detected object from said first confocal point.

8. The multi-focus physiologic sensing device for condensing light of claim 7, wherein a curved surface of each of said first ellipse reflection parts is identical to a curved surface of said second ellipse reflection part.

9. The multi-focus physiologic sensing device for condensing light of claim 2, wherein said lighting elements are arranged on said two second focus points of said second ellipse reflection member.

10. The multi-focus physiologic sensing device for condensing light of claim 7, wherein said lighting elements are arranged on said two second focus points of said second ellipse reflection member.

11. The multi-focus physiologic sensing device for condensing light of claim 1, wherein said lighting elements are red light lighting elements, green light lighting elements, or infrared light lighting elements.

12. The multi-focus physiologic sensing device for condensing light of claim 1, wherein said lighting elements are light emitting diodes (LEDs), surface-mounted-device light-emitting diodes (SMD LEDs), or laser diodes (LDs).

13. The multi-focus physiologic sensing device for condensing light of claim 1, further comprising a casing encasing said lighting elements, said multi-focus condenser and said sensor and exposing said first confocal point.

14. The multi-focus physiologic sensing device for condensing light of claim 11, wherein said infrared light lighting elements emit light having a wavelength of 1000 nm~1700 nm, and said green light lighting elements emit light having a wavelength of 500 nm~560 nm, and said red light lighting elements emit light having a wavelength of 600 nm~700 nm or 900 nm~1000 nm.

15. The multi-focus physiologic sensing device for condensing light of claim 11, wherein said infrared light lighting elements are used to measure blood sugar, and said green light lighting elements are used to measure a heart rate, and said red light lighting elements are used to measure blood oxygen.

* * * * *